US012685588B2

(12) United States Patent
Altmann et al.

(10) Patent No.: US 12,685,588 B2
(45) **Date of Patent: *Jul. 21, 2026**

(54) IRREVERSIBLE ELECTROPORATION (IRE) BASED ON FIELD, CONTACT FORCE AND TIME

(71) Applicant: Biosense Webster (Israel) Ltd., Yokneam (IL)

(72) Inventors: Andres Claudio Altmann, Haifa (IL); Assaf Govari, Haifa (IL); Vadim Gliner, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 655 days.

This patent is subject to a terminal disclaimer.

(21) Appl. No.: 18/301,768

(22) Filed: Apr. 17, 2023

(65) Prior Publication Data

US 2023/0248428 A1 Aug. 10, 2023

Related U.S. Application Data

(63) Continuation of application No. 16/726,312, filed on Dec. 24, 2019, now Pat. No. 11,707,320.

(51) Int. Cl.
*A61B 18/12* (2006.01)
*A61B 18/14* (2006.01)
(Continued)

(52) U.S. Cl.
CPC ..................... *A61B 18/1492* (2013.01); *A61B 2018/00357* (2013.01); *A61B 2018/00613* (2013.01);
(Continued)

(58) Field of Classification Search
CPC .......... A61B 2018/006; A61B 2018/13; A61B 2018/00779; A61B 2018/00678; A61B 2018/00708; A61B 2090/065
See application file for complete search history.

(56) References Cited

U.S. PATENT DOCUMENTS 8,048,067 B2 11/2011 Davalos et al.
8,221,411 B2 7/2012 Francischelli et al.
(Continued)

FOREIGN PATENT DOCUMENTS

CN 106580424 A 4/2017
EP 3117791 A1 1/2017
WO 2018092071 A1 5/2018

OTHER PUBLICATIONS

Office Action from corresponding Chinese Patent Application No. 202010079351.1 dated Aug. 20, 2020.
(Continued)

*Primary Examiner* — Jaymi E Della
(74) *Attorney, Agent, or Firm* — Dergosits & Noah LLP; Todd A. Noah

(57) ABSTRACT

A method and system includes, using a probe, applying irreversible electroporation (IRE) pulses to tissue over a time period to form a lesion in the tissue. A contact force applied to the tissue by the probe is measured over the time period. An IRE index is calculated based on the measured contact force and on a power level of the IRE pulses. Whether a value of the calculated estimated IRE index values has reached the prespecified target IRE index value is determined. Application of the IRE pulses to the tissue is displayed as a graphic and/or alphanumeric data while the estimated IRE index values are being calculated.

15 Claims, 4 Drawing Sheets

(51) Int. Cl.
　　*A61B 18/00* 　　　　(2006.01)
　　*A61B 90/00* 　　　　(2016.01)

(52) U.S. Cl.
　　CPC ............... *A61B 2018/00648* (2013.01); *A61B 2018/00678* (2013.01); *A61B 2018/00708* (2013.01); *A61B 2018/00779* (2013.01); *A61B 2018/00892* (2013.01); *A61B 2090/065* (2016.02)

(56) References Cited

U.S. PATENT DOCUMENTS

| | | | |
|---|---|---|---|
| 10,271,893 B2 | 4/2019 | Stewart et al. | |
| 10,342,598 B2 | 7/2019 | Long et al. | |
| 10,517,670 B2 | 12/2019 | Bar-Tal et al. | |
| 10,531,914 B2 | 1/2020 | Stewart et al. | |
| 2010/0250209 A1 | 9/2010 | Pearson et al. | |
| 2012/0095459 A1 | 4/2012 | Callas et al. | |
| 2012/0209260 A1* | 8/2012 | Lambert | A61B 18/1492 606/41 |
| 2015/0088120 A1 | 3/2015 | Garcia et al. | |
| 2016/0051324 A1 | 2/2016 | Stewart | |
| 2016/0213282 A1* | 7/2016 | Leo | A61B 5/6885 |
| 2017/0014181 A1* | 1/2017 | Bar-Tal | A61B 18/1492 |
| 2019/0030328 A1 | 1/2019 | Stewart et al. | |

OTHER PUBLICATIONS

Office Action from corresponding Chinese Patent Application No. 202010079351.1 dated Nov. 13, 2020.
International Search Report from corresponding International Patent Application No. PCT/IB2020/050683 dated Sep. 18, 2020.
Reddy, MD et al., "Pulsed Field Ablation for Pulmonary Vein Isolation in Atrial Fibrillation," Journal of the American College of Cardiology, 74:3, 2019.
Mujovic et al., "Catheter Ablation of Atrial Fibrillation: An Overview for Clinicians," Adv. Ther. 34: 1897-1917, 2017.
World Health Organization Study: Atrial Fibrillation is a Growing Global Health Concern, Dec. 17, 2013.

\* cited by examiner

IRREVERSIBLE ELECTROPORATION (IRE) BASED ON FIELD, CONTACT FORCE AND TIME

CROSS-REFERENCE TO RELATED APPLICATION

This application is a continuation application of U.S. application Ser. No. 16/726,312, filed Dec. 24, 2019, now U.S. Pat. No. 11,707,320, which is incorporated herein by reference.

FIELD OF THE INVENTION

The present invention relates generally to irreversible electroporation (IRE) of cardiac tissue, and specifically to estimation of the size of a lesion formed during the IRE.

BACKGROUND OF THE INVENTION

Estimation of cardiac radiofrequency (RF) ablation parameters and controlling the RF ablation according to the estimation has been previously proposed in the patent literature. For example, U. S. Patent Application Publication 2017/0014181 describes a method, consisting of ablating tissue for a time period, measuring a contact force applied during the time period, and measuring the power used during the time period. The method further includes ceasing ablating the tissue when a desired size of a lesion produced in the tissue, as estimated using an integral over the time period of a product of the contact force raised to a first non-unity exponent and the power raised to a second non-unity exponent, is reached.

As another example, U.S. Patent Application Publication 2016/0213282 describes a method and apparatus that utilize a force-time integral for real time estimation of lesion size in catheter-based ablation systems. The apparatus measures the force exerted by a contact ablation probe on a target tissue and integrates the force over an energization time of the ablation probe. The force-time integral can be calculated and utilized to provide an estimated lesion size (depth, volume and/or area) in real time. The force-time integral may also account for variations in the power delivered to the target tissue in real time to provide an improved estimation of the lesion size. In one embodiment, the force metric can be used as feedback to establish a desired power level delivered to the probe to prevent steam popping. In still other embodiments, the control system can be adapted to increase irrigation, in addition or in place of decreasing or disabling energization.

SUMMARY OF THE INVENTION

An exemplary embodiment of the present invention provides a method including, using a probe, applying irreversible electroporation (IRE) pulses to tissue over a time period to form a lesion in the tissue. A contact force applied to the tissue by the probe is measured over the time period. An IRE index is calculated based on the measured contact force and on a power level of the IRE pulses. Application of the IRE pulses to the tissue is ceased in response to the calculated IRE index reaching a prespecified target IRE index value.

In some exemplary embodiments, calculating the IRE index includes calculating an integral over the time period of a product of the contact force raised to a first calibrated exponent and the power level raised to a second calibrated exponent.

In some exemplary embodiments, the method further includes presenting the IRE index and the prespecified target IRE index value to a user.

In an exemplary embodiment, the IRE index corresponds to an estimated volume of the lesion. In another exemplary embodiment, the IRE index corresponds to an estimated depth of the lesion. In a further exemplary embodiment, the IRE index corresponds to an estimated diameter of the lesion.

In some exemplary embodiments, the method further includes measuring the power level by measuring a peak voltage of the IRE pulses.

In some exemplary embodiments, the method further includes simulating an electric field produced by the IRE pulses to estimate a planned depth of the lesion.

There is additionally provided, in accordance with another exemplary embodiment of the present invention, a system including a probe and a processor. The probe is configured to apply irreversible electroporation (IRE) pulses to tissue over a time period to form a lesion in the tissue. The processor is configured to (a) measure a contact force applied to the tissue by the probe over the time period, (b) calculate an IRE index based on the measured contact force and on a power level of the IRE pulses, and (c) cease application of the IRE pulses to the tissue in response to the calculated IRE index reaching a prespecified target IRE index value.

BRIEF DESCRIPTION OF THE DRAWINGS

The present disclosure will be more fully understood from the following detailed description of the embodiments thereof, taken together with the drawings, in which.

DETAILED DESCRIPTION OF EMBODIMENTS

Overview

Figure 1:
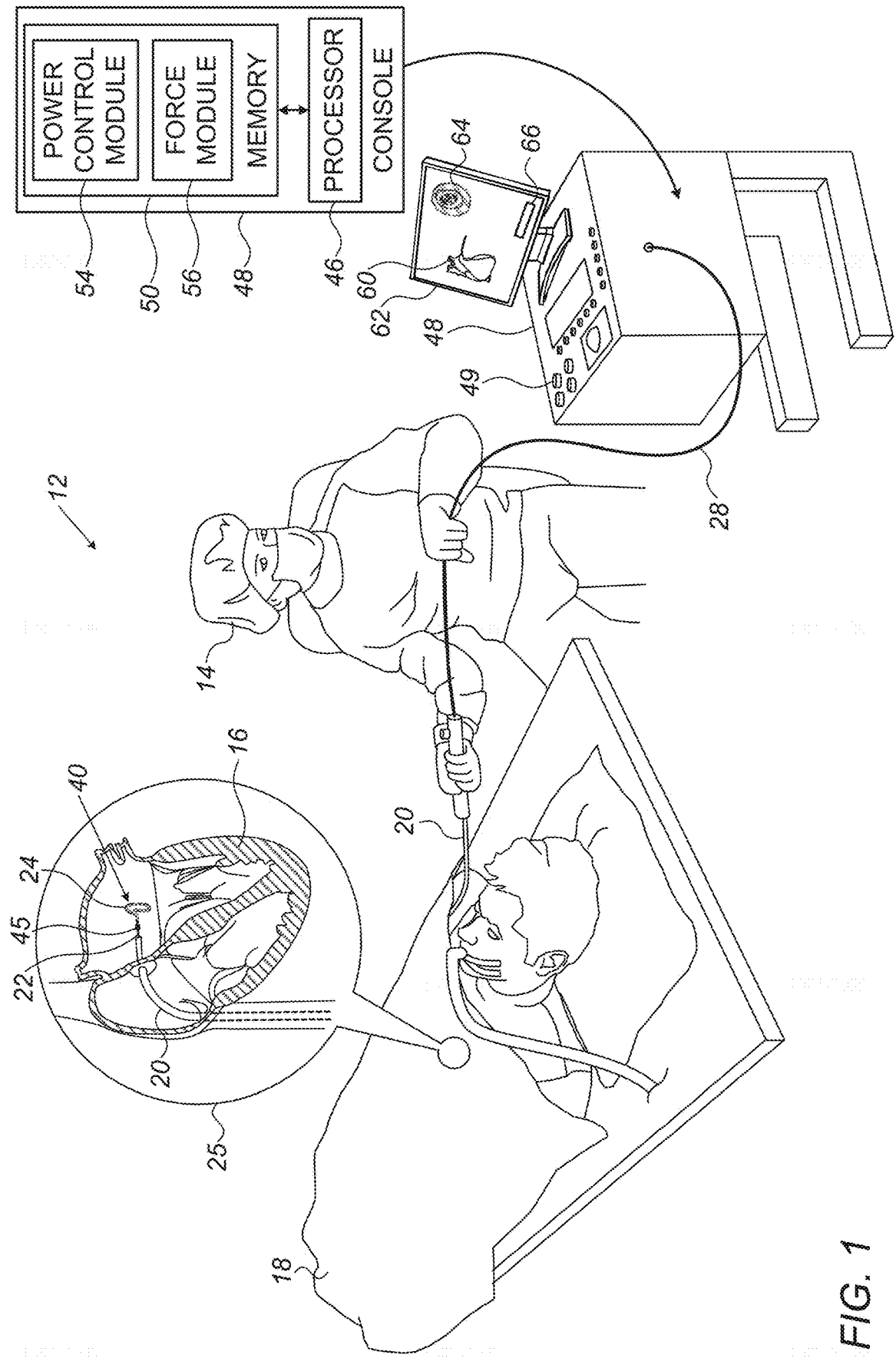
FIG. 1 is a schematic, pictorial illustration of a catheter-based system for irreversible electroporation (IRE) treatment, in accordance with an exemplary embodiment of the present invention.

A lesion in tissue, typically tissue that is part of the heart of a patient undergoing a cardiac procedure, may be produced by a catheter using irreversible electroporation (IRE). The catheter is inserted so that it contacts the tissue, and high voltage bi-polar pulses are applied between catheter electrodes to the tissue, causing cell destruction and production of a lesion.

To predict and control IRE treatment, it would be desired to have a universal and linear IRE scale that corresponds to the size of the lesion. A possible scale can correspond to a size S of a lesion assumed to be proportional to a product of the force F applied by the catheter to the tissue, the power P dissipated during the IRE procedure, and the time T of the procedure. Although the possible scale involves power P, the relation to lesion size is related to IRE pulse generator RMS output current (I), based on the following equation: P=H·I², where H is a constant. This equation applies to all of the discussion below.

Thus, a scale to estimate the size S of the lesion according to this assumption can be given using S from an Eq. 1:

$$S = K \cdot F \cdot P \cdot T \qquad \text{(Eq. 1)}$$

where K is a constant of proportionality, and $$P = H \cdot V_p^2,$$

where $V_p$ is the IRE pulse generator peak output voltage, and the peak electric field in tissue, $E_p$, is proportional to $V_p$. The proportionality constant depends on the type of catheter, including spacing between electrodes.

As is apparent from Eq. 1, an estimate of the size of a lesion given by the equation is linearly proportional to F, to P, and to T, since, in the equation, each of these variables is raised to the power of one; i.e., from Eq. 1 size S is a linear function of F, of P, and of T.

In practice, the relationship between lesion size and F, P, and T is proven to be non-linear, and thus the sought IRE scale would also be non-linear. Following this observation, the exemplary embodiments of the disclosed invention provide a more exact estimate of the size of a lesion from the values of F, P, and T, with a more exact estimate of lesion size given by finding an integral over time of an expression comprising non-linear functions of F, P, and T. The estimate may be applied during IRE of tissue, separate from estimating the volume of the lesion, the depth of the lesion, and/or the diameter of the lesion produced in the tissue, so as to halt IRE when a desired size is reached.

In an exemplary embodiment of the present invention, a universal IRE linear scale, named hereinafter "IRE index," is derived by calculating an integral over the time period of a product of the contact force raised to a first calibrated non-unity exponent and the power raised to a second calibrated non-unity exponent.

In some exemplary embodiments, an IRE index is provided, which is a time integral of the force applied and power dissipated by the IRE pulses. The values of the IRE index (for different size/volume of lesions) are determined experimentally and calibrated. For a given type of cardiac structure, and given tissue characteristics, the value of the IRE index is expected to be a repeatable predictor of lesion size. Furthermore, lesion size for a given value of IRE index may vary due to different structures and tissue characteristics.

In some exemplary embodiments, a physician irreversibly electroporates tissue with a catheter over a time period to form a lesion in the tissue. During the time period measurements are made of a contact force applied by the catheter and the irreversibly electroporative power used for the tissue. Based on the measured contact force and irreversibly electroporative power, the IRE index is derived (e.g., calculated), and irreversibly electroporating the tissue is halted when the calculated IRE index has reached a prespecified target IRE index value. Using the universal and linear IRE index ensures that, when an estimated size reaches a desired size, the IRE treatment can be stopped.

Some exemplary embodiments of the present invention further simulate the electric field produced by the electrodes in an IRE system, and display the values of the fields graphically. Prior to actually generating the IRE pulses, a physician uses the displayed graphic to position the electrodes so that the appropriate fields are applied to destroy tissue. In the exemplary embodiments, a processor may adjust the theoretical fields displayed by taking into account the IRE index, or the contact force of the electrodes with the cells, and/or the proximity of the cells to the electrodes.

By providing an IRE index, a catheter-based IRE treatment can be made safer and more effective.

DETAILED DESCRIPTION

FIG. 1 is a schematic, pictorial illustration of a catheter-based system 12 for irreversible electroporation (IRE) treatment, in accordance with an exemplary embodiment of the present invention. As described below, with reference to the flow chart of FIG. 3, the procedure uses estimates of lesion size that may be derived using the aforementioned IRE index.

The IRE procedure is performed by a physician 14, and, by way of example, the procedure in the description herein below is assumed to comprise IRE of a portion of a myocardium 16 of the heart of a human patient 18.

In order to perform the ablation, physician 14 inserts a probe 20, by way of example, a Lasso catheter (made by Biosense Webster, Irvine, California) into a lumen of the patient, so that a distal end 22 of the probe enters the heart of the patient. As inset 25 shows, distal end 22 comprises multiple electrodes 24 mounted on the outside of an articulated section 40 of distal end 22, the electrodes contacting a location of the myocardium. Distal end 22 also comprises a force sensor 45. Probe 20 also comprises a proximal end 28.

System 12 is controlled by a system processor 46, which is located in an operating console 48 of the system. Console 48 comprises controls 49 which are used by physician 14 to communicate with the processor. During the procedure, processor 46 typically tracks a location and an orientation of distal end 22 of the probe, using any method known in the art. For example, processor 46 may use a magnetic tracking method, wherein magnetic transmitters external to patient 18 generate signals in coils positioned in the distal end. The Carto® system produced by Biosense Webster uses such a tracking method. As another example, a location and an orientation of distal end 22 may be tracked using the Advanced Catheter Location (ACL) system, made by Biosense-Webster, which is described in U.S. Pat. No. 8,456, 182, whose disclosure is incorporated herein by reference. In the ACL system, a processor estimates the respective locations of multiple electrodes 24 based on impedances measured between each of electrodes 24, and a plurality of surface electrodes that are coupled to the skin of patient 18.

The software for processor 46 may be downloaded to the processor in electronic form, over a network, for example. Alternatively or additionally, the software may be provided on non-transitory tangible media, such as optical, magnetic, or electronic storage media. The tracking of distal end 22 is typically displayed on a three-dimensional representation 60 of the heart of patient 18 on a screen 62. The progress of the IRE treatment performed with system 12 is typically also displayed on screen 62, as a graphic 64 and/or alphanumeric data 66.

In order to operate system 12, processor 46 communicates with a memory 50, which has a number of modules used by the processor to operate the system. Thus, memory 50 comprises a power control module 54 and a force module 56. Power control module 54 delivers IRE power to electrodes 24, and also measures the instantaneous power P(t) delivered at a time t, typically by measuring the instantaneous peak voltage $V_p(t)$ delivered by the electrode. If the waveform is fixed, $V_p(t)$ can be determined by measuring an instantaneous RMS voltage $V_{RMS}(t)$. Force module 56 measures an instantaneous contact force CF(t) at time t, by acquiring and evaluating signals from force sensor 45 in distal end 22. Memory 50 may also comprise other modules, such as a temperature-measuring module and an irrigation module. For simplicity, such other modules are not described further in this application. The modules of memory 50 may comprise hardware as well as software elements.

Derivation of an IRE Index

A general estimate of a volume of a lesion that is produced by IRE of tissue can be written as:

$$V(T) = C \int_0^T CF^\alpha(t) P^\beta(t) dt \qquad \text{(Eq. 2)}$$

where
V(T) is the volume of the lesion produced by IRE over a time period T;
C is a constant of proportionality;
CF(t) is a value of the instantaneous contact force, at a time t, applied to the tissue during the ablation;
P(t) is a value of the instantaneous power, at a time t, dissipated during the ablation; and
$\alpha$, $\beta$ are numerical exponents having values not equal to 1 (unity).
Since, as stated above, the power P can be expressed in terms of the peak voltage $V_p$ flowing as $$P = H \cdot V_p^2,$$

Eq. 2 can also be written as:

$$V(T) = C \cdot H \int_0^T CF^\alpha(t) V_p^{2\beta}(t) dt \qquad \text{(Eq. 2a)}$$

where H is a constant, and where $V_p(t)$ is a value of the instantaneous peak voltage applied at a time t.
In the following description of results the units used for each of the variables in evaluating Eq. 2 and Eq. 2a are assumed, by way of example, to be as in Table I:

TABLE I

| Variable | Units |
|---|---|
| V(T) | mm$^3$ |
| CF(t) | g (grams) |
| P(t) | W ( watts) |
| $V_p(t)$ | V (volts) |
| t, T | s (seconds) |
| C | $\dfrac{mm^3}{g \cdot W \cdot s}$ |
| $\alpha$, $\beta$ | dimensionless |

Alternative equations to Eq. 2 and Eq. 2a are Eq. 3 and Eq. 4 are shown below:

$$\text{Depth}^\gamma(T) = C \cdot H \int_0^T CF^\alpha(t) V_p^{2\beta}(t) dt \qquad \text{(Eq. 3)}$$

where each of the terms are as defined above with respect to Eq. 2 and Eq. 2a, and where Depth is the depth of the lesion in mm, and $\gamma$ is a numerical exponent not equal to 1 (unity).

$$\text{Diam}^\delta(T) = C \cdot H \int_0^T CF^\alpha(t) V_p^{2\beta}(t) dt \qquad \text{(Eq. 4)}$$

where each of the terms are as defined above with respect to Eq. 2 and Eq. 2a, and where Diam is the diameter of the lesion in mm, and $\delta$ is a numerical exponent not equal to unity.

Approximations to the Equations

Eqs. 2, 2a, 3 and 4 may be approximated by assuming that CF or P or I do not vary over the time period T. The following description describes approximations for Eq. 3, but those having ordinary skill in the art will be able to apply similar approximations for Eq. 2 and Eq. 4.

For simplicity, in the following description Eq. 3 is used with power rather than current:

$$\text{Depth}^\gamma(T) = C \int_0^T CF^\alpha(t) P^\beta(t) dt \qquad \text{(Eq. 3')}$$

If P is assumed to have a fixed value over the time period T of the ablation, then Eq. 3' can be rewritten:

$$\text{Depth}^\gamma(T) = CP^\beta \int_0^T CF^\alpha(t) dt \qquad \text{(Eq. 5)}$$

If CF is almost fixed or if $\alpha \approx 1$ then $$\int_0^T CF^\alpha(t) dt \cong ACF^\alpha \cdot T \qquad \text{(Eq. 6)}$$

where ACF is an average value of CF over time T.
Substituting Eq. 6 into Eq. 5 gives:

$$\text{Depth}^\gamma = C \cdot ACF^\alpha \cdot P^\beta \cdot T \qquad \text{(Eq. 7)}$$

Values of C, $\alpha$, $\beta$, and $\gamma$
Taking logs of both sides of Eq. 7 gives:

$$\text{Log(Depth)} = \frac{1}{\gamma}\text{Log}(C) + \frac{\alpha}{\gamma}\text{Log}(ACF) + \frac{\beta}{\gamma}\text{Log}(P) + \frac{1}{\gamma}\text{Log}(T) \qquad \text{(Eq. 8)}$$

The values of C, $\alpha$, $\beta$, and $\gamma$ in Eq. 8 can be derived experimentally and calibrated, including using linear regression analysis to evaluate C, $\alpha$, $\beta$, and $\gamma$.

The integral $$\int_0^T CF^\alpha(t)P^\beta(t)dt$$

is herein termed the IRE index, and is referred to as $I_{FTP\_IRE}$. Thus, $$I_{FTP\_IRE} = \int_0^T CF^\alpha(t)P^\beta(t)dt \qquad \text{(Eq. 9)}$$

Figure 2A:
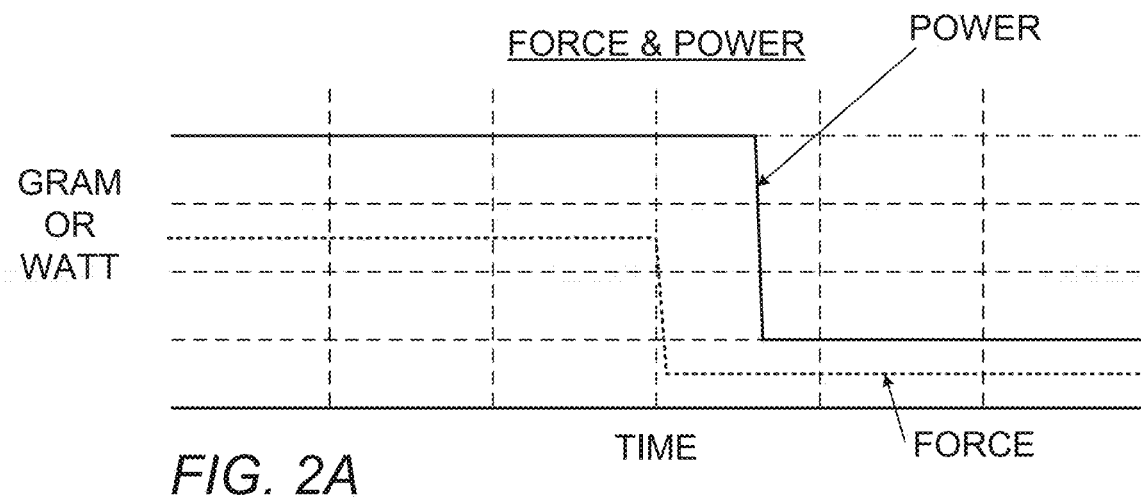
FIGS. 2A, 2B, and 2C are graphs of force, power, depth and IRE index vs. time, according to an exemplary embodiment of the present invention.
Figure 2B:
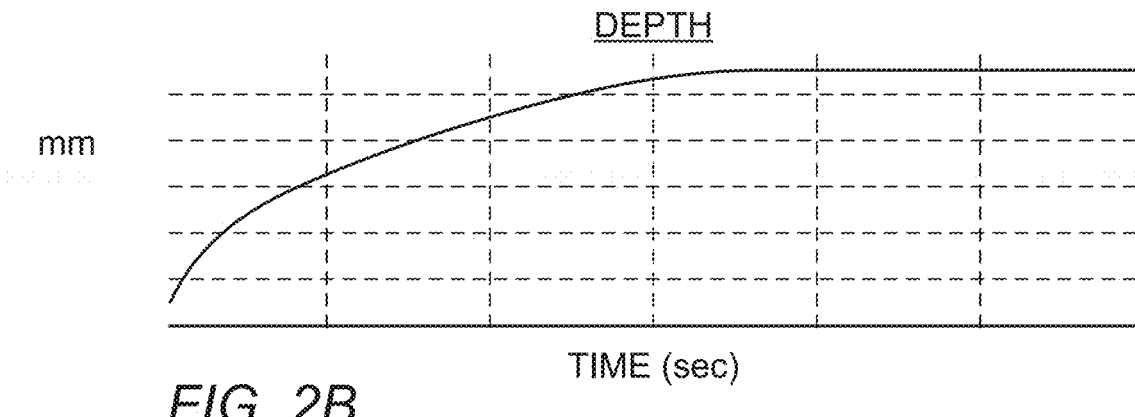
Figure 2C:
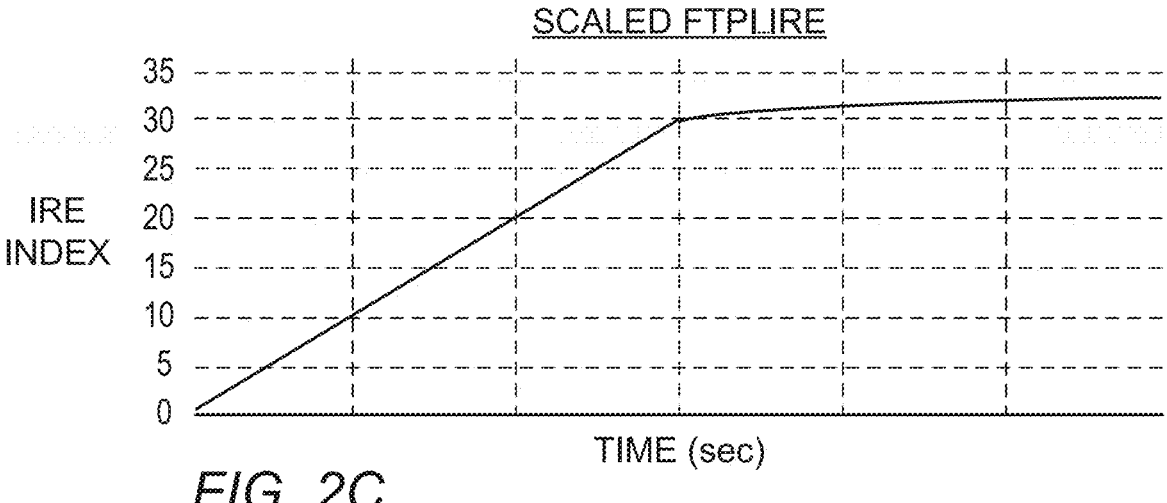

FIGS. 2A, 2B, and 2C are schematic graphs of force, power, depth, and FTP_IRE vs. time, according to an embodiment of the present invention. The graphs illustrate how estimated depth and the IRE index may look when both the power and the force change. The graph of IRE index vs. time shows that the estimated IRE index is designed to increase linearly with duration of IRE treatment.

For a given type of cardiac structure and given tissue characteristics, the value of the IRE index is expected to be a repeatable predictor of lesion size. Furthermore, lesion size for a given value of ablation index may vary due to different structures and tissue characteristics.

Figure 3:
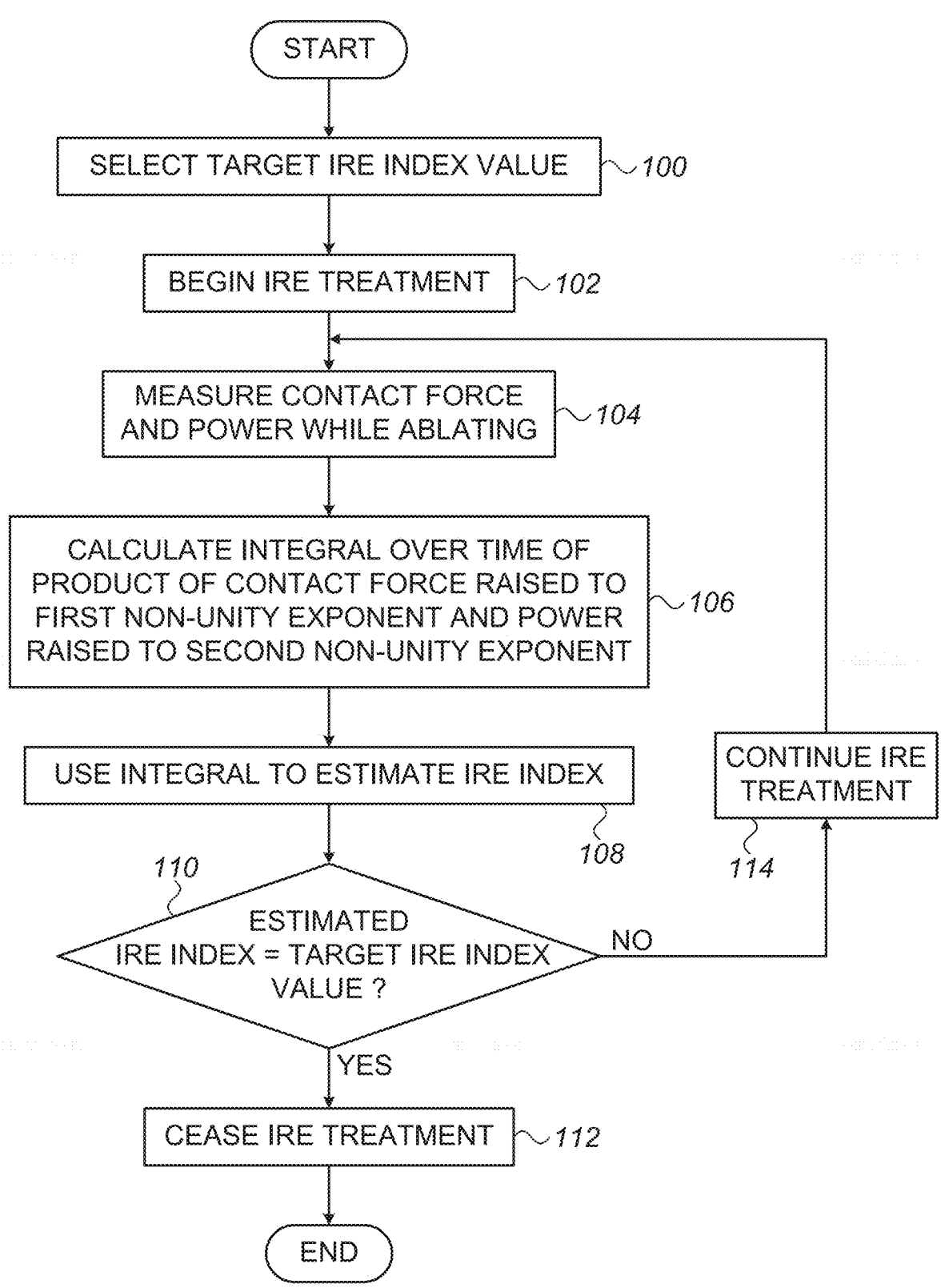
FIG. 3 is a flow chart that schematically illustrates a method for IRE treatment, performed using the system of FIG. 1, according to an exemplary embodiment of the present invention.

FIG. 3 is a flow chart that schematically illustrates a method for IRE treatment, performed using system 12 of FIG. 1, according to an exemplary embodiment of the present invention. In an initial step 100, the physician selects a target IRE index value to form a planned lesion. By way of example, the physician may select a target IRE index value that yields a desired depth that is in the range of 1 mm-5 mm. In addition, the physician selects values of C, α, β, and γ to be used in an equation for depth estimation to be used, herein assumed to be Eq. 3.

In a start IRE treatment step 102, the physician uses controls 49 to select a voltage waveform having a given peak voltage, which yields a nominal power to be delivered by power control module 54. Typically, the resulting power is in the range of several milliwatts, although a power outside this range may result. After the peak nominal voltage has been selected, the physician uses controls 49 to begin the IRE treatment.

In a measuring step 104, as the ablation is being performed, power control module 54 measures the instantaneous power P(t) dissipated by electrodes 24, which may be different from the derived nominal power. In addition, force module 56 measures the instantaneous contact force CF(t) on distal end 22.

In a calculation step 106, as the IRE treatment proceeds, processor 46 calculates, on a recurring basis, the value of the integral used in Eq. 5, i.e., the value of ablation index $I_{FTP\_IRE}$ in Eq. 9. In an IRE index estimation step 108, the processor calculates a value of the estimated IRE index, using equation Eq. 9.

In a decision step 110, the processor checks if the estimated IRE index is equal to the target IRE index value. If a positive decision is returned in a final step 112, the processor halts the IRE treatment. If a negative decision is returned, the processor, in a continuing ablation step 114, continues to apply IRE treatment, and the flow chart returns to measuring step 104.

Figure 4:
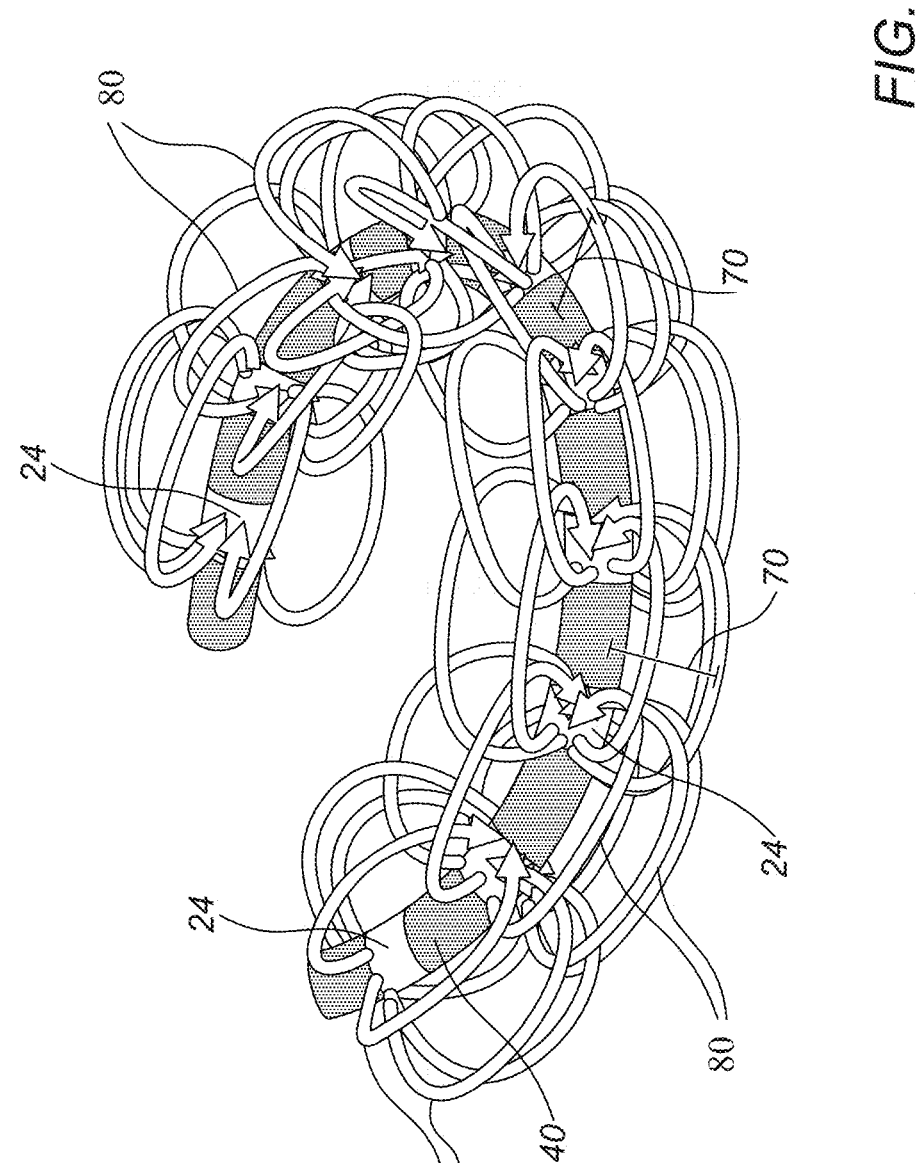
FIG. 4 is a diagram that schematically illustrates a simulation of an electric field produced by the electrodes of the catheter of FIG. 1 when driven with IRE pulses, according to an exemplary embodiment of the present invention.

To further estimate a planned depth of a lesion formed by the IRE pulses, the disclosed technique further comprises simulating an electric field produced by the IRE pulses. FIG. 4 is diagram that schematically illustrates a simulation of an electric field produced by 24 electrodes of the catheter of FIG. 1 when driven with IRE pulses, according to an exemplary embodiment of the present invention. FIG. 4 shows the RMS valued theoretical field lines 80 generated by bipolar electrodes on lasso 40 catheter.

Prior to actually generating the IRE pulses, physician 14 uses the displayed graphic to position electrodes 24 so that the appropriate fields are applied to the tissue cells that it is desired to destroy.

As seen, the simulated field penetrates a depth 70 into space, and depth 70 can be used to plan the strength of IRE pulses (e.g., peak voltage, $V_p$), using, for example, Eq. 3b.

While not shown in FIG. 4, some exemplary embodiments may adjust the theoretical fields displayed by taking into account the contact force of the electrodes with the cells, and/or the proximity of the cells to the electrodes.

Although the exemplary embodiments described herein mainly address cardiac applications, the methods and systems described herein can also be used in other medical applications, such as in neurology, renal denervation, and otolaryngology.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method of applying irreversible electroporation pulses (IRE) to tissue to form a lesion, the method comprising:
   receiving a prespecified target IRE index value, wherein the prespecified target IRE index value is not a size of the lesion but a repeatable predictor of the size of the lesion, the size of the lesion comprising a volume, a depth and a diameter of the lesion;
   causing the IRE pulses to be applied to the tissue over a time period to form the lesion;
   causing instantaneous contact forces and instantaneous power levels of the IRE pulses applied to the tissue to be measured over the time period;
   calculating, on a recurring basis, estimated IRE index values using an integral over the time period of a product of the measured instantaneous contact forces, respectively, raised to a first calibrated non-unity exponent and the measured instantaneous power levels of the IRE pulses, respectively, raised to a second calibrated non-unity exponent, the calculated estimated IRE index values corresponding respectively to an estimated volume, an estimated depth and an estimated diameter of the lesion;
   causing progress of the application of the IRE pulses to the tissue over the time period to be displayed as a graphic and/or alphanumeric data while the estimated IRE index values are being calculated;

determining whether a value of the calculated estimated IRE index values has reached the prespecified target IRE index value, and causing the application of the IRE pulses to the tissue to continue when the value of the calculated estimated IRE index values has not reached the prespecified target IRE index value.

2. The method according to claim 1, further comprising causing the application of the IRE pulses to the tissue to cease in response to the value of the calculated estimated IRE index values reaching the prespecified target IRE index value.

3. The method according to claim 1, further comprising causing the calculated estimated IRE index values and the prespecified target IRE index value to be presented to a user.

4. The method according to claim 1, further comprising causing the instantaneous power levels to be measured by measuring a peak voltage of the IRE pulses.

5. The method according to claim 1, further comprising causing an electric field produced by the IRE pulses to be simulated.

6. A system for applying irreversible electroporation pulses (IRE) to tissue to form a lesion, the system comprising:

one or more processors; and a non-transitory computer readable medium storing a plurality of instructions, which when executed, cause the one or more processors to:

receive a prespecified target IRE index value, wherein the prespecified target IRE index value is not a size of the lesion but a repeatable predictor of the size of the lesion, the size of the lesion comprising a volume, a depth and a diameter of the lesion;

cause the IRE pulses to be applied to the tissue over a time period to form the lesion;

cause instantaneous contact forces and instantaneous power levels of the IRE pulses applied to the tissue to be measured over the time period;

calculate, on a recurring basis, estimated IRE index values using an integral over the time period of a product of the measured instantaneous contact forces, respectively, raised to a first calibrated non-unity exponent and the measured instantaneous power levels of the IRE pulses, respectively, raised to a second calibrated non-unity exponent, the calculated estimated IRE index values corresponding respectively to an estimated volume, an estimated depth and an estimated diameter of the lesion;

cause progress of the application of the IRE pulses to the tissue over the time period to be displayed as a graphic and/or alphanumeric data while the estimated IRE index values are being calculated;

determine whether a value of the calculated estimated IRE index values has reached the prespecified target IRE index value, and cause the application of the IRE pulses to the tissue to continue when the value of the calculated estimated IRE index values has not reached the prespecified target IRE index value.

7. The system according to claim 6, wherein the plurality of instructions further cause the one or more processors to cause the application of the IRE pulses to the tissue to cease in response to the value of the calculated estimated IRE index values reaching the prespecified target IRE index value.

8. The system according to claim 6, wherein the plurality of instructions further cause the one or more processors to cause the calculated estimated IRE index values and the prespecified target IRE index value to be presented to a user.

9. The system according to claim 6, wherein the plurality of instructions further cause the one or more processors to cause the instantaneous power levels to be measured by measuring a peak voltage of the IRE pulses.

10. The system according to claim 6, wherein the plurality of instructions further cause the one or more processors to cause an electric field produced by the IRE pulses to be simulated.

11. A computer program product, comprising a non-transitory computer-readable medium having computer-readable program code embodied therein to be executed by one or more processors, the program code including instructions to:

receive a prespecified target IRE index value, wherein the prespecified target IRE index value is not a size of the lesion but a repeatable predictor of the size of the lesion, the size of the lesion comprising a volume, a depth and a diameter of the lesion;

cause the IRE pulses to be applied to the tissue over a time period to form the lesion;

cause instantaneous contact forces and instantaneous power levels of the IRE pulses applied to the tissue to be measured over the time period;

calculate, on a recurring basis, estimated IRE index values using an integral over the time period of a product of the measured instantaneous contact forces, respectively, raised to a first calibrated non-unity exponent and the measured instantaneous power levels of the IRE pulses, respectively, raised to a second calibrated non-unity exponent, the calculated estimated IRE index values corresponding respectively to an estimated volume, an estimated depth and an estimated diameter of the lesion;

cause progress of the application of the IRE pulses to the tissue over the time period to be displayed as a graphic and/or alphanumeric data while the estimated IRE index values are being calculated;

determine whether a value of the calculated estimated IRE index values has reached the prespecified target IRE index value, and cause the application of the IRE pulses to the tissue to continue when the value of the calculated estimated IRE index values has not reached the prespecified target IRE index value.

12. The computer program product according to claim 11, wherein the program code includes further instructions to cause the application of the IRE pulses to the tissue to cease in response to the value of the calculated estimated IRE index values reaching the prespecified target IRE index value.

13. The computer program product according to claim 11, wherein the program code includes further instructions to cause the calculated estimated IRE index values and the prespecified target IRE index value to be presented to a user.

14. The computer program product according to claim 11, wherein the program code includes further instructions to cause the instantaneous power levels to be measured by measuring a peak voltage of the IRE pulses.

15. The computer program product according to claim 11, wherein the program code includes further instructions to cause an electric field produced by the IRE pulses to be simulated.

* * * * *